United States Patent

Crossley et al.

[11] Patent Number: 5,001,131
[45] Date of Patent: Mar. 19, 1991

[54] PYRIDINE DERIVATIVES

[75] Inventors: Roger Crossley, Reading; Albert Opalko, Maidenhead, both of United Kingdom

[73] Assignee: John Wyeth & Brother Limited, Maidenhead, England

[21] Appl. No.: 367,530

[22] Filed: Jun. 16, 1989

[30] Foreign Application Priority Data

Jun. 17, 1988 [GB] United Kingdom ............... 8814459

[51] Int. Cl.$^5$ ..................... A61K 31/44; A61K 31/47
[52] U.S. Cl. ................................. 514/299; 514/290; 514/297; 514/311; 514/312; 514/313
[58] Field of Search ............... 514/290, 297, 299, 311, 514/312, 313

[56] References Cited

U.S. PATENT DOCUMENTS 4,576,949  3/1986  Smith .................................. 514/277

FOREIGN PATENT DOCUMENTS 0161867  11/1985  European Pat. Off. .
2171995   9/1986  United Kingdom .

Primary Examiner—Thurman K. Page
Assistant Examiner—G. S. Kishore
Attorney, Agent, or Firm—George Tarnowski

[57] ABSTRACT

The invention provides a method of relieving inflammation in a mammal inflicted with an imflammatory disease which method comprises treating said mammal with a therapeutically effective amount of a compound of formula I

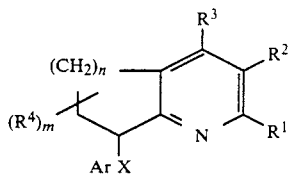

wherein $R^1$, $R^2$ and $R^3$ represent hydrogen, loweralkyl, cycloloweralkyl, loweralkoxy, carboxy, hydroxyloweralkyl, halogen, haloloweralkyl, loweralkoxycarbonyl, aryl or aralkyl or 7–12 carbon atoms, or $R^1$ and $R^2$ taken together, or $R^2$ and $R^3$ taken together form a 5,6, or 7 membered ring with the carbon atoms to which they are attached, which ring may be saturated or unsaturated and unsubstituted or substituted by loweralkyl or loweralkoxy, $R^4$ represents hydrogen, loweralkyl, loweralkoxy, aryl or aralkyl of 7–12 carbon atoms, n is 1,2 or 3, m is 1,2 or 3, Ar represents phenyl which may be substituted by halogen, loweralkyl, loweralkoxy, haloloweralkyl, haloloweralkoxy, nitro, amino; cyano, loweralkylamino, diloweralkylamino, carboxy, loweralkoxycarbonyl, loweralkanoyl, loweralkanoylamino, aryl or aminoloweralkyl, X is $NHSO_2$, NH, NHCO—, CH(OH), O, CO, S, SO or $SO_2$, or a pharmaceutically acceptable salt thereof.

7 Claims, No Drawings

PYRIDINE DERIVATIVES

The invention relates to pyridine derivatives with fused rings for instance tetrahydroquinoline and homologous compounds.

GB Patent Specification 2148284A discloses 5,6,7,8-tetrahydroquinolines in which the 8 position carries the substituent $R^6R^7C(OH)$ where $R^6$ and $R^7$ represent hydrogen, alkyl, cycloalkyl, aralkyl or aryl groups and corresponding 7-substituted cyclopenta [b] and 9-substituted cyclohepta [b] pyridine compounds. These compounds are chemical intermediates. We have now found that such compounds where $R^6$ is hydrogen and $R^7$ is aryl exhibit anti-inflammatory activity in standard test procedures. We have also found that analogous compounds carrying other substituents at the 8-position and the corresponding 7-substituted cyclopenta[b] and 9-substituted cyclohepta [b] pyridines also exhibit anti-inflammatory activity.

European Patent application 161867 discloses 5,6,7,8-tetrahydroquinolines carrying at the 8-position a variety of substituents including the group —$CH_2 X^2$, where $X^2$ is inter alia optionally substituted phenyl. The corresponding cyclopenteno-b-pyridines are also disclosed. These compounds are said to have utility in the treatment of asthma, chronic bronchitis, cystic fibrosis, psoriasis or inflammatory bowel disease. J. Org.chem 1981 46(10) 2059-65 discloses 5,6,7,8-tetrahydro-8-benzenesulphonyl-quinoline.

The invention provides compounds of formula I

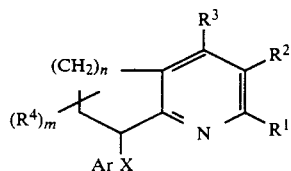

wherein $R^1$, $R^2$, $R^3$ represent hydrogen, alkyl, cycloalkyl, alkoxy, carboxy, hydroxyalkyl, halogen, haloalkyl, alkoxycarbonyl, aryl or aralkyl, or $R^1$ and $R^2$ taken together or $R^2$ and $R^3$ taken together form a 5,6, or 7 membered ring with the carbon atoms to which they are attached, which ring may be saturated or unsaturated and substituted or unsubstituted, $R^4$ represents hydrogen, alkyl, alkoxy, aryl or aralkyl, n is 1, 2 or 3, m is 1,2 or 3, Ar represents phenyl which may be substituted by one or more substituents commonly used in pharmaceutical chemistry e.g. halogen (such as chlorine, bromine or fluorine), alkyl, alkoxy, haloalkyl eg trifluoromethyl, or haloalkoxy (eg. $CHF_2O$—, $CF_3CH_2O$—), nitro, amino, cyano, alkylamino, dialkylamino, carboxy, alkoxycarbonyl, acyl, acylamino, eg. alkanoylamino, aryl (eg phenyl) or aminoalkyl, X is $NHSO_2$, NH,. NHCO—, CH(OH), O, CO, S, SO or $SO_2$ or a pharmaceutically acceptable salt thereof, for use as anti-inflammatory agents.

The preferred alkyl substituents, or alkyl portions of other substituents eg. alkoxy, or haloalkyl, are lower alkyl groups of 1 to 6 carbon atoms which may have a straight or branched chain eg. methyl, ethyl, n and iso propyl and n- s- and t-butyl. $R^4$ may be a gem dialkyl group eg. gem dimethyl. Preferably $R^1$, $R^2$, $R^3$ and $R^4$ are selected from hydrogen and loweralkyl.

An aralkyl group is preferably arylloweralkyl of 7–12 carbon atoms eg. phenylalkyl wherein the alkyl portion is a lower alkyl group as defined above. An acyl group is preferably lower alkanoyl of 2 to 7 carbon atoms.

Cycloalkyl groups are preferably cycloloweralkyl especially those having from 4 to 6 carbon atoms eg. cyclobutyl, cyclopentyl or cyclohexyl.

A preferred group of compounds of formula I are those in which X is CO and Ar is 3,4-dimethylphenyl. Another preferred group are those in which n is 3 and X is CH(OH).

When $R^1$ and $R^2$ taken together, or $R^2$ and $R^3$ taken together form a ring, the ring may be substituted by loweralkyl or loweralkoxy.

The compounds of formula I, form salts with pharmaceutically acceptable acids including hydrochloric, hydrobromic, hydroiodic, sulphuric, nitric, phosphoric, methanesulphonic, acetic, maleic, citric, fumaric, tartaric, malonic or formic acid. These salts may be prepared by standard procedures.

Some compounds of formula I in which X is CH(OH) are described generally in GB Patent 2148284 although none are exemplified in this patent specification.

Compounds of formula I, where X is CO may be prepared from corresponding compounds of formula II

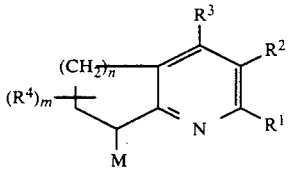

where M is lithium, sodium or potassium by treatment with a nitrile ArCN optionally with the prior addition of a triialkylsilyl halide, eg. trimethylsilyl chloride, where Ar is as defined above. The reaction with the silyl halide proceeds according to the following scheme:

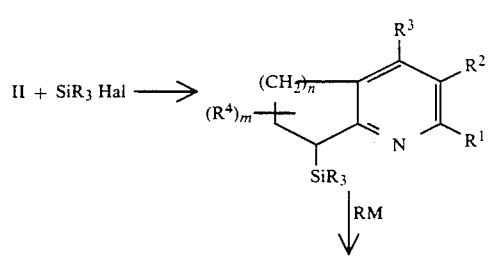

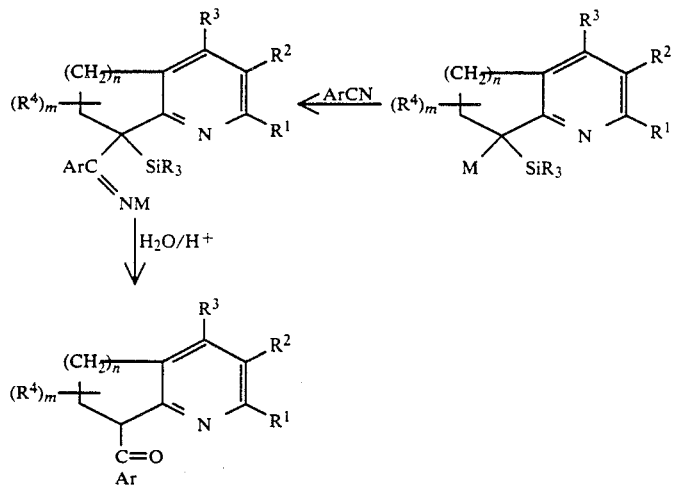

Alternatively a compound of formula II may be treated with a compound ArCOY where Y is a leaving group eg. halogen or alkoxy to give a compound of formula I.

The products of formula I where X is CO may be selectively reduced, eg. with a standard reducing agent, eg. sodium borohydride to give a compound of formula I in which X is CHOH. Alternatively compounds of formula I where X is CHOH may be prepared by treating a metal compound of formula II with an aldehyde of formula ArCHO where Ar is as defined above.

Starting compounds of formula II are described in GB Patents 1463670, 1465651, 1458148 and 1495993 or may be prepared by analogous methods to those described in one or more of these patent specifications.

Compounds of formula I in which X is $NHSO_2$ may be prepared by treating a corresponding amino compound of formula III

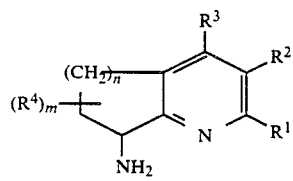

with an aryl sulphonyl halide of formula $ArSO_2$ Hal where Hal is chlorine, bromine, or iodine, preferably chlorine.

The starting compounds of formula III are described in GB Patent 1463582 or may be made by analogous methods.

Compounds of formula I where X is NH may be prepared by selectively reducing a corresponding compound of formula IV

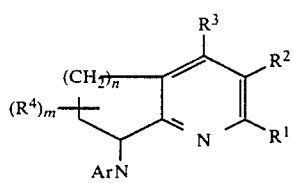

with eg. a borohydride reducing agent such as sodium borohydride. The starting compounds of formula IV may be prepared by condensing an aryl amine $ArNH_2$ with an oxo compound of formula V

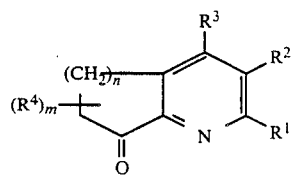

The compounds of formula V may be prepared as described in GB Patents 1432378 or 1460457 or by analogous methods.

Compounds of formula I in which X is S may be prepared by treating a compound of formula VI

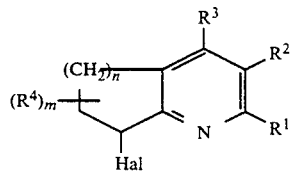

where $R^1$, $R^2$, $R^3$, $R^4$, m and n are as defined above and Hal is chlorine, bromine or iodine with a thiol of formula ArSH, or an alkali metal salt thereof, where Ar is as defined above. The starting compounds of formula VI are described in GB Patent 1463583 or may be made by analogous methods. Alternatively compounds of formula I where X is S may be prepared by treating a compound of formula II above with a thiol ArSH or disulphide $(ArS)_2$.

Compounds of formula I in which X is O may be prepared by treating a compound of formula VI with a phenol ArOH where Ar is as defined above.

Compounds of formula I in which X is NHCO may be prepared by treating an amine of formula III as defined above with an acid halide of formula ArCOHal where Hal is chlorine, bromine or iodine but is preferably chlorine.

Compounds of formula I in which X is SO or $SO_2$ may be prepared by treating a compound of formula I where X is S with a per acid eg perbenzoic acid or a substituted perbenzoic acid such as m-chloroperbenzoic acid.

Certain compounds of formula I are novel compounds and the invention includes these compounds per se namely those in which X is $NHSO_2$, NH, NHCO, O CO, S and SO, and those where X is $SO_2$ except when Ar is unsubstituted phenyl, n is 2 and $R^1$, $R^2$, $R^3$ and $R^4$ are hydrogen.

Some compounds in which X is CHOH are also novel and these are included per se, in particular compounds of formula I in which X is CHOH and Ar is 3 methylphenyl, 4-methyl- phenyl or 3,4 dimethylphenyl.

Compounds of formula I exhibit anti-inflammatory activity as determined by standard test procedures.

The invention includes a method of relieving inflammation in a mammal inflicted with an inflammatory disease which method comprises treating said mammal with a therapeutically effective amount of a compound of formula I as defined above, or a pharmaceutically acceptable salt thereof.

METHODS

Assessment of Acute Anti-inflammatory Activity Using Rat Carrageenan Edema.

Groups of six male Sprague-Dawley rats (Charles River), weighing between 150–165g, are used in these experiments. Drugs are administered p.o. in 0.5% methylcellulose (400 centipoise). One hour after administering drugs or vehicle, 0.1ml of 1% carrageenan is injected subplantar into the right hind paw. Right hind paw volumes (ml) are measured prior to carrageenan injection using a mercury plethysmograph (ie. zero time reading). After three hours, the right hind paw volumes are re-measured and paw edema is calculated for each rat by subtracting the zero time reading from the three hour reading and the percent change in paw edema is calculated. The Dunnett's test is used to determine statistical significance ($P < 0.05$).

Rat Adjuvant Arthritis (prophylactic model, chronic inflammation)

Groups of ten male Lewis rats (Charles River), weighing between 150-170g, are injected s.c. into the right hind paw with dessiccated *Mycobacterium butyricum* (0.5 mg/0.1ml) suspended in light mineral oil. Drugs are administered orally in 0.5% methylcellulose from day 0 to 15 (except weekends). Both hind paw volumes (ml) are measured by mercury plethysmography at the time of injection of adjuvant (day 0). Paw volumes are measured on day 4 (injected paw only) and on day 16 (uninjected paw) to determine the nonspecific and immunologically-induced inflammation, respectively. Drug effects are expressed as a percentage change from vehicle-treated arthritic controls.

The invention includes a pharmaceutical composition comprising a compound of formula I and a pharmaceutically acceptable carrier.

The pharmaceutical formulations include solids and liquids. Any suitable carrier known in the art can be used to prepare the pharmaceutical composition. In such a composition, the carrier is generally a solid or liquid, or a mixture of a solid and a liquid.

Solid form compositions include powders, granules, tablets, capsules (eg. hard and soft gelatin capsules), suppositories and pessaries. A solid carrier can be, for example, one or more substances which may also act as flavouring agents, lubricants, solubilisers, suspending agents, fillers, glidants, compression aids, binders, effervescent excipients or tablet-disintegrating agents; it can also be an encapsulating material. In powders the carrier is a finely divided solid which is in admixture with the finely divided active ingredient. In tablets the active ingredient is mixed with a carrier having the necessary compression properties in suitable proportions and compacted in the shape and size desired. The powders and tablets preferable contain up to 99%, eg. from 10 to 80% preferably 25 to 75% of the active ingredient. Suitable solid carriers include, for example, calcium phoshate, magnesium stearate, talc, sugars, lactose, dexterin, starch, gelatin, cellulose, methyl cellulose, sodium carboxymethyl cellulose, polyvinylpyrrolidone, low melting waxes and ion exchange resins. The term "composition" is intended to include the formulation of an active ingredient with encapsulating material as carrier to give a capsule in which the active ingredient (with or without other carriers) is surrounded by the carrier, which is thus in association with it. Similarly cachets are included.

Liquid form compositions include, for example, suspensions, emulsions, syrups and elixirs. The active ingredient, for example, can be suspended in a pharmaceutically acceptable liquid carrier such as water, an organic solvent, a mixture of both or pharmaceutically acceptable oils or fats. The liquid carrier can contain other suitable pharmaceutical additives such as solubilizers, emulsifiers, buffers, preservatives, sweeteners, flavouring agents, suspending agents, thickening agents, colours, viscosity regulators, stabilisers or osmo-regulators. Suitable examples of liquid carriers for oral administration include water (particularly containing additives as above eg. cellulose derivatives, preferably sodium carboxymethyl cellulose solution), alcohols (including monohydric alcohols and polyhydric alcohols eg. glycerol and glycols) and their derivatives, and oils (eg. fractionated coconut oil and arachis oil).

Preferably the pharmaceutical composition is in unit dosage form, eg. as tablets or capsules. In such form, the composition is sub-divided in unit doses containing appropriate quantities of the active ingredient; the unit dosage forms can be packaged compositions, for example, packeted powders. The unit dosage form can be, for example, a capsule or tablet itself, or it can be the appropriate number of any such compositions in package form. The quantity of the active ingredient in a unit dose of composition may be varied or adjusted from 10mg or less to 500mg or more, according to the particular need.

The following examples illustrate the invention.

EXAMPLE 1

5,6,7,8-Tetrahydro-3-methyl-8-(4-methylbenzenesulphonyl amino)quinoline

8-Amino-5,6,7,8-tetrahydro-3-methyl-quinoline (3.07g) was dissolved in $CH_2Cl_2$ [(250ml) and 4-methylbenzenesulphonyl-chloride (2.68g) was added in $CH_2Cl_2$ (25ml) followed by triethylamine (25ml) in $CH_2Cl_2$ (25ml). The reaction mixture was stirred at room temperature until t.l.c. showed all the starting material to have reacted. The solvent was removed under reduced pressure and the residue was dissolved in 2N.HCl (200ml) and extracted with $Et_2O$ (2×100ml). The acid solution was then basified with solid $K_2CO_3$ and was extracted with $CH_2Cl_2$ (3×100ml). The extracts were dried ($MgSO_4$) and evaporated to low volume under reduced pressure. The residue was treated with $Et_2O$/HCl to give a white solid which was recrystallised from EtOH to give 5,6,7,8-tetrahydro-3-methyl- 8-(4-methylbenzenesulphonylamino) quinoline hydrochloride (2.1g). mp. 214° C. decomp. (Found: C,58.3; H,6.2; N,7.7. $C_{17}H_{21}N_2SO_2Cl$ requires: C,58.0; H,6.0; N,7.8%).

EXAMPLE 2

5,6,7,8-Tetrahydro-8-(4-methylphenylamino)-3-methylquinoline 6,7-Dihydro-3-methyl-quinolin-8(5H)-one (3.2g,0.02m) and p-toluidine (2.2g, 0.02m) in cyclohexane (50ml) were refluxed for 3h. and the water produced was collected by means of a Dean and Stark apparatus. The solvent was removed under reduced pressure and the residue of 6,7-dihydro-3-methyl-8(5H)-(4-methylphenylimino)quinoline dissolved in ethanol (50ml). Sodium borohydride (0.5g) was added and the mixture stirred at room temperature for 1h, then acidified with 2M hydrochloric acid and evaporated. The residue was treated with 2M sodium hydroxide and extracted with chloroform. The combined chloroform extracts were washed with water, dried ($MgSO_4$) and evaporated under reduced pressure. The residue was recrystalled from hexane to give 5,6,7,8-tetrahydro-8-(4-methylphenylamino)-3-methylquinoline (1.7g, 34%) m.p. 83°-5° C. (Found C, 81.05; H, 8.2; N, 11.2 $C_{17}H_{20}N_2$ requires C, 80.9; H, 8.0; N, 11.1%).

EXAMPLE 3

5,6,7,8-Tetrahydro-4-methyl-8-(4-methylbenzoyl) quinoline

A solution of 5,6,7,8-tetrahydro-4-methylquinoline (1.47g, 0.01m) in THF (3ml) was added to a mixture of butyl lithium in hexane (1.36M solution, 7.5ml, 0.01m) in THF (15ml), maintained below 0° C. After 0.5h the mixture was blown over into a solution of trimethylsilyl chloride (1.1g, 0.01m) in THF (5ml), maintained below 10° C to give 5,6,7,8-tetrahydro-4-methyl-8-trimethylsilyl quinoline.

After 0.5h., a solution of butyl lithium in hexane (1.36M, 7.5ml, 0.01m) was added at 0° C. and the mixture stirred for 0.5h, then 4-methylbenzonitrile (1.4g, 0.012m) in THF (5ml) was added rapidly. After 0.5h the mixture was quenched with 2M hydrochloric acid (30ml) and the aqueous phase separated. The aqueous extract was basified with solid potassium carbonate and extracted with chloroform. The mixture was purified by chromatography on silica using ether as eluant. The isolated product was dissolved in ether and treated with ethereal HCl to give 5,6,7,8-tetrahydro-4-methyl-8-(4-methylbenzoyl)quinoline hydrochloride 1.5g, 49%) mp. 240°-242° C. (Found C, 71.6; H, 6.7; N, 4.6;$C_{18}H_{19}N$ 0.HCl requires C, 71.4; H, 6.7; N, 4.65%).

EXAMPLE 4

5,6,7,8-Tetrahydro-4-methyl-8-(3,4-dimethylbenzoyl)-quinoline

A mixture of 5,6,7,8-Tetrahydro-4-methylquinoline (2.2g, 0.017m) and THF (5ml) was added to a mixture of butyl lithium in hexane (1.36M solution, 11.2ml, 0.017m) and THF (15ml) maintained below 0° C. After 0.5h the mixture was blown over into a solution of trimethylsilyl chloride (1.65g, 0.017m) in THF (10ml), maintained below 10° C.

After 0.5h, a 1.36M solution of butyl lithium (11.2ml, 0.017m) was added at 0.° C. and the mixture stirred at this temperature for a further 0.5h. A solution of 3,4-dimethylbenzonitrile (2.6g, 0.02m) in THF (20ml) was added rapidly and after 0.5h a solution of 2M hydrochloric acid (40ml) was added and the aqueous phase separated. This was basified with solid potassium carbonate and the mixture extracted with ether. The mixture was purified by chromatography on silica using ether as eluant. The isolated product was dissolved in ether and acidified with ethereal HCl to give 5,6,7,8-tetrahydro-4-methyl-8-(3,4-dimethylbenzoyl)quinoline hydrochloride (2.5g, 53%) m.p. 237°-9° C. (Found; C,72.25; H, 7.0;N, 4.4 $C_{19}H_{21}NO$.HCl requires C, 71.8; H, 7.1; N, 4.3%).

EXAMPLE 5

R* S* and R* R*
5,6,7,8-Tetrahydro-3,7,7-Tetrahydro-3,7,7-trimethyl-1(4-methylphenyl)quinolin-8-yl-methanol 5,6,7,8-Tetrahydro-3,7,7-trimethylquinoline (3g) in tetrahydrofuran (50ml) was treated with a 1.36M solution of butyl lithium in hexane (13ml) at 0° C. After 5 minutes a solution of.4-tolualdehyde (3g) in tetrahydrofuran (3ml) was added rapidly and the mixture stirred at room temperature for 0.25h. Water and ether were added and the organic phase separated. The ether phase was extracted with 2M hydrochloric acid and this was basified with solid potassium carbonate and extracted with ether. The combined ether extracts were dried ($MgSO_4$) and evaporated to give 5.5g of yellow oil (2 isomers by t.l.c. This was purified by medium pressure chromatography on silica using di-isopropyl ether as eluant to give the first component which was recrystalised from di-isopropyl ether to give R* S* 5,6,7,8-tetrahydro-3,7,7-trimethyl 1-(4-methylphenyl)-quinolin-8-yl-methanol (1.2g, 24%) m.p. 111°-113° C. (Found: C, 81.3,H, 8.9; N, 4.85 $C_{20}H_{25}NO$ requires C, 81.3; H, 8.5; N, 4.7%).

Further elution with di-isopropyl ether gave R* R* 5,6,7,8-tetrahydro-3,7,7-trimethyl 1-(4-methylphenyl)-quinolin-8-yl-methanol. This was recrystallised from di-isopropyl ether to give a white solid m.p. 93°-95° C.

EXAMPLE 6

R* S* and R*R*1- (6,7,8,9-Tetrahydro-5H-cyclohepta[b] pyrid-9-yl)-1-(4methylphenyl)-methanol.

6,7,8,9-Tetrahydro-5H-cyclohepta[b] pyridine (7.4g 0.05m) in tetrahydrofuran (100ml) was cooled to $-10°$ C. and treated with a 1.57M solution of n-butyl lithium in n-hexane (32ml), then stirred at $-10°$ C. for a further 0.5h. 4-Tolualdehyde (10g, 0.083m) in tetrahydrofuran (10ml) was added rapidly and the mixture allowed to warm to room temperature, then water and ether were added. The combined ether extracts were treated with 2N hydrochloric acid and the separated aqueous acid extract was basified with solid sodium carbonate and then extracted with chloroform. The combined chloroform solutions were washed with water, dried ($MgSO_4$) and evaporated to give an oil. This was purified by chromatography using silica columns eluted with DIPE or chloroform. The purification was monitored by t.l.c. using DIPE and chloroform on silica plates or samples were silylated with 1-(trimethylsilyl)-imidazole and injected on a g.l.c. (injection temp. 200° C.) with a 25 meter BPI column, running a temperature programme from 120° to 300° C. at 10° C./min., then isothermal and carrier gas helium at 10psi. The products were isolated and these were converted into the hydrochloride salts by dissolving in ether and treating with ethereal HCl to give R*, S* 1-(6,7,8,9-tetrahydro-5H-cyclohepta-[b] pyrid-9-yl)-1-(4-methylphenyl) methanol hydrochloride (retention time 16.72 min, 1.4g, 9%) m.p. 205°-7° C. (Found: C, 71.4;H, 7.5; N, 4.6; $C_{18}H_{21}NO.HCl$ requires C, 71.2;H, 7.3; N, 4.6%). R*, R* 1-(6,7,8,9-tetrahydro-5H-cyclohepta[b] pyrid-9yl)-1-(4-methylphenyl) methanol, hydrochloride, three quarter hydrate (retention time 16.63 min, 1.7g, 11%) m.p. 216°-7° C. (Found C, 68.6; H, 7.3; N, 4.35, $C_{18}H_{21}NO.HCl$. $0.75H_2O$ requires C, 68.1; H, 7.5; N, 4.4%).

EXAMPLE 7

R* R* and R* S*1-(4-Methylphenyl)-1-(5,6,7,8-tetrahydro -3-methyl-quinoline-8-yl) methanol.

To a solution 5,6,7,8-tetrahydro-3-methylquinoline (5.88g, 0.04m) in tetrahydrofuran (30ml) at −20° C., under nitrogen, was added a 1.6M solution of n-butyl lithium in n-hexane (25ml) and left to stir at −20° C. for 0.25h. 4-methylbenzaldehyde (4.32g, 0.04m) in tetrahydrofuran (15ml) was added and the mixture allowed to warm to room temperature. Water was added and then ether and the organic phase separated and extracted with 2N hydrochloric acid. The aqueous acid extract was basified with potassium carbonate and extracted with chloroform, which was separated, dried ($MgSO_4$) and evaporated. The oil was purified by chromatography on silica using di-isopropyl ether as eluant to give R*,R* 1-(4-methylphenyl)-1-(5,6,7,8-tetrahydro-3-methyl quinoline-8-yl) methanol. This was recrystallised from n-hexane to give a white solid (4.26g, 40%) m.p. 91°-3° C.

(Found : C, 81.1; H, 8.0; N, 5.2; $C_{18}H_{21}NO$ requires C, 80.9; H, 7.9; N, 5.2%).

The second component was R*, S*-1-(4-methylphenyl)-1-(5,6,7,8-tetrahydro-3-methylquinoline-8-yl) methanol. This was recrystallised from di-isopropyl ether to give a white solid (1.75g, 16%) m.p. 140°-2° C.

(Found C, 80.55; H, 8.1; N, 5.2, $C_{18}H_{21}NO$ requires C, 80.9; H, 7.9; N, 5.2%).

EXAMPLE 8

5,6,7,8-Tetrahydro-3-methyl-8-phenylthioquinoline n-Butyl lithium in n-hexane (90ml 1.25M) was added to a stirred mixture of 5,6,7,8-tetrahydro-3-methylquinoline (7.4g) and diisopropylamine (10ml) in tetrahydrofuran (200ml) at −78° C. The reaction was stirred for 30 minutes then a solution of diphenyl disulphide (10.9g) in tetrahydrofuran (100ml) was added dropwise over 45 minutes. The mixture was stirred for 1 hour while allowing it to warm up to room temperature. The mixture was quenched with water, concentrated and partitioned between ether and water. The organic layer was washed with 2M sodium hydroxide. The organic layer was extracted into dilute HCl (2M), basified and extracted with $CH_2Cl_2$, dried ($MgSO_4$) and concentrated to obtain 12.85g of the title compound. The solid was converted to the hydrochloride and recrystallised from ethyl acetate/methanol mp 173°-176° C.

(Found C, 65.4; H 6.4; N 5.1. $C_{16}H_{17}NS$ HCl requires C 65.85, H 6.22, N, 4.8%

EXAMPLE 9

5,6,7,8-Tetrahydro-3-methyl-8-phenylsulphinylquinoline

To a stirred solution of 5,6,7,8-tetrahydro-3-methyl-8-phenylthioquinoline (3.8g, 15M Mols) in $CH_2Cl_2$ (30ml) at 0° C. was added m - chloroperbenzoic acid (3g, 15 M mols) in $CH_2Cl_2$ (20ml). The reaction mixture was stirred for 30 minutes then the mixture was washed with dilute NaOH (2M), dried ($MgSo_4$) and concentrated. The residue was triturated with ether and the the resulting precipitate collected by filtration to obtain the title compound 3g which was recrystallised from $CH_2Cl_2$/ether mp 123°-128° C. (decomp) (Found C, 70.73, H6.52, N 4.94; $C_{16}H_{17}NOS$ requires C, 70.82, H 6.31, N 5.16%). The filtrate was concentrated and chromatographed to yield 0.9g of the other diastereoisomer.

EXAMPLE 10

5,6,7,8-Tetrahydro-3-methyl-8-phenylsulphonylquinoline.

A solution of m-chloroperbenzoic acid (1.4g) in dichloromethane (25ml) was added to a stirred solution of 5,6,7,8-tetrahydro-3-methyl-8-phenylsulphinylquinoline (1.87g) and trifluoroacetic acid (1.2ml) in dichloromethane (25ml). After stirring at ambient temperature for 1h, the reaction mixture was washed with 2M sodium hydroxide, dried over magnesium sulphate and evaporated to a solid. After chromatography on silica eluting with ether the product was recrystallised from diisopropylether affording white crystals, mp 84°-86° C.

(Found C, 66.8; H,6.0; N5.2; $C_{16}H_{17}NO_2S$ requires C, 66.9; H, 6.0; N,4.9%.)

EXAMPLE 11

8-Benzoyl-5,6,7,8-tetrahydro-3-methylquinoline

To a solution of 5,6,7,8-tetrahydro-3-methylquinoline (3g) in THF (20ml) at 0° C under nitrogen was added 1.7 molar n-BuLi/hexane solution (12ml) followed by benzonitrile (2ml). The mixture was stirred at ambient temperature ½h then 2N HCl was added and the mixture was stirred a further 15 min. The aqueous layer was separated and washed with ether then basified and extracted with chloroform. The extracts were dried ($MgSO_4$) and evaporated. The product was purified by chromatography, first on fluorisil with chloroform and them on silica with 2% $MeOH/CHCl_3$ as eluant. The product was converted into the hydrochloride in propan-2-ol with a $Et_2O/HCl$ solution and allowed to crystallise to give 8-benzoyl-5,6,7,8-tetrahydro-3-methylquinoline hydrochloride (1.5g) m.p. 137°-40° C. (Found: C, 70.7; H, 6.5; N, 4.8. $C_{17}H_{17}NO.HCl$ requires C, 70.95; H, 6.3; N, 4.9%.

EXAMPLE 12

5,6,7,8-Tetrahydro-8-phenylthioquinoline

Thiophenol (1.6g) was added to a solution of NaOH (1.8g) in ethanol (30ml) and the resulting solution was treated with a solution of 8-chloro-5,6,7,8-tetrahydroquinoline hydrochloride (3g) in ethanol (10ml). The mixture was left at ambient temperature overnight, filtered through kieselghur and evaporated. The residue was dissolved in ethanol, acidified with ethereal HCl, filtered and evaporated. The resulting solid was recrystallised from propan-2-ol-acetone to give 5,6,7,8-tetrahydro-8-phenylthioquinoline hydrochloride, hemihydrate (0.85g) mp. 184°-5° C. (Found: C,62.9; H,6.0; N,4.8 $C_{15}H_{15}NS.HCl\frac{1}{2}H_2O$ requires C,62.8; H,6.0; N, 4.9%).

EXAMPLE 13

5,6,7,8-Tetrahydro-3-methyl-8-(4-nitrobenzamido)quinoline

To 8-amino-5,6,7,8-tetrahydro-3-methylquinoline (4.5g, 2.27 M moles) in $CH_2Cl_2$ was added 4-nitrobenzoylchloride (4.2g, 2.26Mmoles) followed by sufficient triethylamine to clear the solution and then form a new precipitate. This material was left overnight and then the solvent removed. The residue was taken up in 2M .HCl and washed with ethyl acetate. The aquous layer was then basified with $Na_2CO_3$ and extracted with chloroform. The organic solution was dried ($MgSO_4$) and evaporated under reduced pressure to give a residue which was treated with $Et_2O/HCl$ to give a white solid identified by infra-red and nmr specroscopy as the hydrochloride of the title compound.

EXAMPLE 14

5,6,7,8-Tetrahydro-8-(3,4-dimethylbenzoyl)quinoline 5,6,7,8-Tetrahydroquinoline (7.2g 0.054M) was dissolved in THF (50ml) and cooled to 0° C. 35ml of a solution of n-butyl lithium (1.6M in hexane) was added. The mixture was left for 20 minutes then a solution of 3,4,-dimethyl-benzonitrile (7g 0.053M) in THF (50ml) was added. The mixture was allowed to stand for 30 minutes them $2^M$ HCl (100ml) was added. The mixture was allowed to stand for 16 hours after which the resulting yellow crystals were filtered off and washed with isopropyl alcohol then ether to give 6.17g of the title compound as the hydrochloride. The mother liquids were diluted with 2M HCl and extracted with hexane. A small quantity of solid was obtained filtered off and washed . with isopropyl alcohol then ether to give a further 2.2g of the title compound hydrochloride dihydrate m.p. 236°-7° C.

(Found: C, 67.3; H,7.4; N, 4.25; $C_{18}H_{19}NO$, HCl. $2H_2O$ requires C, 67.55; H, 7.2; N, 4.15%)

EXAMPLE 15

5,6,7,8-Tetrahydro-8-(3-methylbenzoyl)quinoline 5,6,7,8-Tetrahydroquinoline (13.3g) in THF (100ml) was treated with 65ml n-butyl lithium in hexane (1.6M) and left for 45 minutes. 3-Methylbenzonitrile (12.5g) was added and the mixture allowed to stand for ½ hour. 2N HCl (100ml) was then added. The reaction mixture was extracted into and washed with hexane and then the aqueous layer was basified ($Na_2CO_3$) and extracted into chloroform. The extract was dried ($MgSo_4$) and evaporated. The residue ca 10g was purified by column chromatography using dichloromethane then ethyl acetate as eluent to give a partial separation.

The residue was dissolved in isopropyl alcohol and treated with $Et_2O/HCl$ to give a gum which was recrystallised from isopropyl alcohol to give the hydrochloride of the title compound (2.25g) m.p. 211°-3° C. (Found; C, 70.9; H, 6.5; N, 4.8; $C_{17}H_{17}NO$ HCl requires C, 70.95; H, 6.3; N 4.9%)

EXAMPLE 16

8-Benzoyl-5,6,7,8-tetrahydroquinoline 5,6,7,8-Tetrahydroquinoline (5g) in THF (50ml) at 0° C. was treated with n-butyl lithium in hexane (25ml of 1.6M solution) and the mixture left for 15 minutes. Benzonitrile (5ml) was then added and the mixture left for 1½ hours. The reaction mixture was quenched with 40ml 2M HCl and washed with hexane and then basified ($Na_2CO_3$). The product was extracted into chloroform and the extract dried ($MgSo_4$). Removal of the solvent gave a residue which was dissolved in ether and filtered through Keiselguhr. The ether solution was purified on a silica column eluting with ethyl acetate. Evaporation of the solvent gave a residue which was treated with $HCl/Et_2O$ to give the hydrochloride of the title compound m.p. 205°-7° C. (Found C, 67.8; H, 6.1; N, 4.95 $C_{16}H_{15}NO$ requires C, 68.0; H, 5.8; N, 4.9%)

EXAMPLE 17

R*R* and R*S*, 1-(4-methylphenyl)-1-(1,2,3,4,5,6,7,8octahydroacridin-4-yl)methanol 1,2,3,4,5,6,7,8-Octahydroacridine (0.5g) in THF (10ml) was cooled to 0° C. and was treated with 1.44M nBuli (1.4ml). After 10 mins 4-tolualdehyde (0.32g) was added in THF (5ml). After 25 mins the reaction mixture was quenched by addition of 2MHCl (25ml) and this reaction mixture was left to stir 16h. The mixture was washed with ethyl acetate, the aqueous layer was basified ($Na_2CO_3$) and extracted into chloroform. This organic layer was dried ($MgSO_4$) and evaporated under reduced pressure. This residue was dissolved in a small volume of isopropyl alcohol and was treated with ethereal hydrogen chloride to give the product as the hydrochloride, and identified by infra red and nmr spectroscopy.

PHARMACOLOGICAL ACTIVITY

| Product of Example | | Rat[a] car | Dev[b] a a |
|---|---|---|---|
| 1 | | −33 | +77 |
| 2 | | −33.5 | +58 |
| 3 | | −12 | +19 |
| 4 | | −25 | −50 |
| 5 | | −19 | −39 |
| 6 | R*S* | −33 | −42 |
| 6 | R*R* | −26 | −32 |
| 7 | R*R* | −33 | +49 |
| 7 | R*S* | −15 | −3 |
| 8 | | −21 | −27 |
| 9 | | −25 | +13 |
| 10 | | −22 | −2 |

[a]Rat carrageenan edema % change at 50 mg/Kg p.o. (3 hr edema).
[b]Rat adjuvant arthritis, % change at 30 mg/Kg p.o. (left paw at day 16).

What is claimed is:

1. A method of relieving inflammation in a mammal inflicted with an inflammatory disease which method comprises treating said mammal with a therapeutically effective amount of a compound of formula I

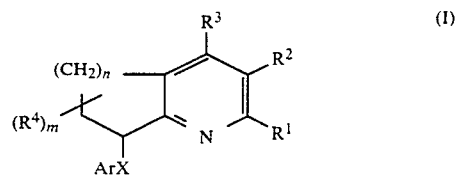

wherein $R^1$, $R^2$ and $R^3$ represent hydrogen, loweralkyl, cycloloweralkyl, loweralkoxy, carboxy, hydroxyloweralkyl, halogen, haloloweralkyl, loweralkoxycarbonyl, aryl or aralkyl of 7–12 carbon atoms, or $R^1$ and $R^2$ taken together, or $R^2$ and $R^3$ taken together form a 5, 6, or 7 membered ring with the carbon atoms to which they are attached, which ring may be saturated or unsaturated and unsubstituted or substituted by loweralkyl or loweralkoxy, $R^4$ represents hydrogen, loweralkyl, loweralkoxy, aryl or aralkyl or 7-12 carbon atoms, n is 1, 2 or 3, m is 1, 2 or 3, Ar represents phenyl which may be substituted by halogen, loweralkyl, loweralkoxy, haloloweralkyl, haloloweralkoxy, nitro, amino, cyano, loweralkylamino, diloweralkylamino, carboxy, loweralkoxycarbonyl, loweralkanoyl, loweralkanoylamino, aryl or aminoloweralkyl, X is $NHSO_2$, NH, NHCO—, CH(OH), O, CO, S, SO or $SO_2$, with the proviso that X is other than S, when $R^1$, $R^2$, $R^3$ and $R^4$ are all hydrogen, or a pharmaceutically acceptable acid addition salt thereof.

2. A method as claimed in claim 1, wherein $R^1$, $R^2$, $R^3$ and $R^4$ are selected from hydrogen and loweralkyl.

3. A method as claimed in claim 1, wherein Ar is 3,4-dimethylphenyl and X is CO.

4. A method as claimed in claim 1, wherein n is 3, and X is CHOH.

5. A method as claimed in claim 4, wherein Ar is phenyl or phenyl substituted by one or two methyl groups.

6. A pharmaceutical composition comprising a compound of formula I as defined in claim 1, or a pharmaceutically acceptable acid addition salt thereof and a pharmaceutically acceptable carrier.

7. A composition as claimed in claim 6, in unit dosage form.

* * * * *